United States Patent [19]

Muller et al.

[11] Patent Number: 5,068,334

[45] Date of Patent: Nov. 26, 1991

[54] PHARMACEUTICAL COMPOSITIONS CONTAINING QUINOLIN-2,5-DIONES, NEW QUINOLIN-2,5-DIONES AND PROCESSES FOR THE PREPARATION THEREOF

[75] Inventors: Erich Muller, Biberach; Josef Nickl, deceased, late of Biberach, by Erma Nickl, executor; Armin Heckel, Biberach; Gunther Engelhardt, Biberach, all of Fed. Rep. of Germany

[73] Assignee: Karl Thomae GmbH, Biberach an Der Riss, Fed. Rep. of Germany

[21] Appl. No.: 413,369

[22] Filed: Sep. 27, 1989

Related U.S. Application Data

[63] Continuation-in-part of Ser. No. 322,602, Mar. 13, 1989, abandoned.

[30] Foreign Application Priority Data

Mar. 11, 1988 [DE] Fed. Rep. of Germany ....... 3808136

[51] Int. Cl.$^5$ .......................................... C07D 215/227
[52] U.S. Cl. .................................. 546/157; 546/158; 546/108; 549/287
[58] Field of Search .................. 546/157, 158, 108; 549/287

[56] References Cited

FOREIGN PATENT DOCUMENTS 76104787 3/1976 Japan .................................... 546/158

OTHER PUBLICATIONS

Mosti et al., J. Heterocyclic Chem. 22 1503 (1985).
Pettit et al., J. Org. Chem 33(3) 1968, pp. 1089–1092.
Ruangsiyanand et al., Chem. Ber. 103 2403–2410 (1970).

*Primary Examiner*—Mukund J. Shah
*Assistant Examiner*—Edward C. Ward
*Attorney, Agent, or Firm*—D. E. Frankhouser; M-E. M. Timbers; A. R. Stempel

[57] ABSTRACT

This invention relates to pharmaceutical compositions containing quinolin-2,5-diones of formula

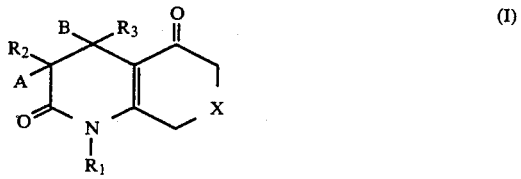

(I)

wherein A, B, $R^1$ to $R^3$ and X are defined hereinbelow, some of which are novel, which compounds have valuable pharmacological properties, particularly analgesic antipyretic and/or antiphlogistic effects, to new intermediates and processes for preparing them.

1 Claim, No Drawings

PHARMACEUTICAL COMPOSITIONS CONTAINING QUINOLIN-2,5-DIONES, NEW QUINOLIN-2,5-DIONES AND PROCESSES FOR THE PREPARATION THEREOF

This is a Continuation-In-Part of application Ser. No. 322,602 filed on Mar. 13, 1989 now abandoned.

Quinolin-2,5-diones have already been described in the literature without any mention whatever of their pharmacological properties (see Arch. Pharm. 308, 588-594 (1975), J. Het. Chem. 22, 1503-1509 (1985), J. Org. Chem. 33, 1089-1092 (1968), Eur. J. Med. Chem. 14, 499-506 (1979), Chem. Ber. 103, 2403-2410 (1970), C. A. 67, 99689, Bull. Soc. Chim. Belge 88. 671-676 (1979), J. Org. Chem. 46, 3719-3721 (1981), Tetrahedron Letters 1965, 2441-2444, Tetrahedron Letters 1967, 2563-2566 and J. Chem. Soc., Perkin Trans. 1 1984, 287-290).

Japanese laid-open specification 76/32568 also describes, inter alia, 5-(3-amino-2-hydroxy-propoxy)-3,4-dihydrocarbostyrile derivatives substituted in the one-position by an ethyl or allyl group, although the 1-ethyl- and 1-allyl5-oxo-hexahydro-carbostyriles necessary for preparing them are not described explicitly.

It has now been found that the quinolin-2,5-diones of formula

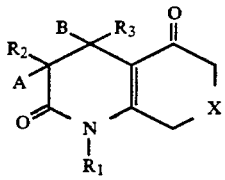

and, if they contain an optically active carbon atom, optically active antipodes thereof, have valuable pharmacological properties, particularly an analgesic, antipyretic and/or antiphlogistic effect.

In formula I above:

A and B each represent a hydrogen atom or together represent a carbon-carbon bond, $R^1$ represents a hydrogen atom, an alkyl group with 1 to 3 carbon atoms optionally substituted by a phenyl, fluorophenyl, chlorophenyl or bromophenyl group, by a carboxy group or by an alkoxycarbonyl group with a total of 2 to 4 carbon atoms, an alkyl group with 4 to 6 carbon atoms, a cycloalkyl group with 3 to 6 carbon atoms, an alkenyl or alkynyl group with 3 to 5 carbon atoms, an alkyl group with 2 or 3 carbon atoms substituted in the 2-or 3-position by a hydroxy, alkoxy or alkylmercapto group, wherein the alkoxy or alkylmercapto substituent may contain from 1 to 3 carbon atoms, a phenyl group optionally substituted by a halogen atom or by an alkyl or alkoxy group with 1 to 3 carbon atoms in the alkyl part, or a tetrahydrofurfuryl group;

$R^2$ represents a hydrogen atom or an alkyl group with 1 to 3 carbon atoms, $R^3$ represents a hydrogen atom, a trifluoromethyl, phenyl or alkyl group with 1 to 3 carbon atoms or $R^2$ and $R^3$ together represent an n-alkylene group with 3 to 5 carbon atoms; and X represents a methylene group optionally substituted by one or two alkyl groups each having 1 to 3 carbon atoms.

The quinolin-2,5-diones which are new are those wherein if A and B together represent another carbon-carbon bond, $R^2$ represents an alkyl group with 1 to 3 carbon atoms and $R^1$, $R^3$ and X are defined as hereinbefore or $R^1$ has the meanings given for $R^1$ hereinbefore with the exception of the hydrogen atom and the methyl and ethyl groups, and $R^2$, $R^3$ and X are defined as hereinbefore or, if A and B each represents a hydrogen atom, $R^1$ has the meanings given for $R^1$ hereinbefore with the exception of the hydrogen atom, the methyl group and the benzyl group, and $R^2$, $R^3$ and X are defined as hereinbefore or $R^2$ represents an alkyl group with 2 or 3 carbon atoms and $R^1$, $R^3$ and X are defined as hereinbefore.

The present invention thus relates to the new pharmaceutical compositions containing a compound of formula I which are suitable for controlling pain, fever and inflammation and for controlling cold symptoms, the new quinolin-2,5-diones of formula I above and processes for the preparation thereof.

As examples of definitions of the groups $R^1$, $R^2$, $R^3$ and X mentioned hereinbefore:

$R^1$ may represent a hydrogen atom, a methyl, ethyl, n-propyl isopropyl, n-butyl, isobutyl, n-pentyl, n-hexyl, cyclopropyl, cyclobutyl, cyclopentyl, cyclohexyl, allyl, n-but-2-enyl, n-but-3-enyl, n-pent-2-enyl, n-pent-3-enyl, propargyl, n-but-2-ynyl, n-but-3-ynyl, n-pent-2-ynyl, n-pent-3ynyl, 2-methyl-n-but-2-enyl, benzyl, fluorobenzyl, chlorobenzyl, bromobenzyl, 1-phenylethyl, 2-phenylethyl, 3-phenylpropyl, 2-(chlorophenyl)-ethyl, carboxymethyl, 1-carboxy-ethyl, 2-carboxyethyl, 1-carboxy-n-propyl, 2-carboxy-n-propyl, 3-carboxy-propyl, methoxycarbonylmethyl, 1-ethoxycarbonyl-ethyl, 2-isopropoxycarbonyl-ethyl, 3-ethoxycarbonyl-n-propyl, 2-hydroxyethyl, 2-hydroxy-n-propyl, 2-hydroxy-1-methyl-ethyl, 2-methoxy-ethyl, 3-ethoxy-n-propyl, 2-n-propoxy-1-methyl-ethyl, 2-methylmercapto-ethyl, 2-ethylmercapto-n-propyl, 2-isopropylmercapto-1-methylethyl, 3-methyl-mercapto-n-propyl, phenyl, fluorophenyl, chlorophenyl, bromophenyl, hydroxyphenyl, methylphenyl, ethylphenyl, isopropylphenyl, methoxyphenyl, ethoxyphenyl, n-propoxy-phenyl or tetrahydrofurfuryl group, $R^2$ may represent a hydrogen atom, a methyl, ethyl, n-propyl or isopropyl group, $R^3$ may represent a hydrogen atom, a methyl, ethyl, n-propyl, isopropyl, trifluoromethyl or phenyl group or $R^2$ and $R^3$ may together represent the n-propylene, n-butylene or n-pentylene group and X may represent a methylene, methyl-methylene, dimethylmethylene, methyl-ethyl-methylene, diethyl-methylene or n-propyl-methylene group.

The following compounds, which are covered by the scope of this invention but not described explicitly in the Examples, will now be mentioned by way of example:

1-isopropyl-3,4,7,8-tetrahydro-2,5(1H,6H)-quinolinedione, 1-n-butyl-3,4,7,8-tetrahydro-2,5(1H,6H)-quinolinedione, 1-allyl-3,4,7,8-tetrahydro-2,5(1H,6H)-quinolinedione and 1-propargyl-3,4,7,8-tetrahydro-2,5(1H,6H)-quinolinedione.

However, preferred compounds of general formula I mentioned hereinbefore are those wherein A and B each represent a hydrogen atom or together represent another carbon-carbon bond, $R^1$ represents a hydrogen atom, an alkyl group with 1 to 4 carbon atoms, an ethyl group substituted in the 2-position by a hydroxy, methoxy, methylmercapto or phenyl group, a phenyl group optionally substituted by a fluorine, chlorine or bromine atom or by a methyl or methoxy group, a cyclohexyl, 3-methoxy- propyl, allyl, propargyl, carboxymethyl, methoxy- carbonylmethyl, benzyl, chlorobenzyl or tetrahydro- furfuryl group, $R^2$ represents a hydrogen atom or a methyl group, $R^3$ represents a hydrogen atom, a methyl, ethyl, trifluoromethyl or phenyl group or $R^2$ and $R^3$ together represent an n-propylene or n-butylene group and X represents a methylene, methyl-methylene or dimethylmethylene group, whilst the new quinolin-2,5-diones are those wherein, if A and B together represent another carbon-carbon bond, $R^2$ represents a methyl group and $R^1$, $R^3$ and X are defined as hereinbefore or $R^1$ has the meanings given for $R^1$ hereinbefore with the exception of the hydrogen atom and the methyl and ethyl groups, and $R^2$, $R^3$ and X are defined as hereinbefore or, if A and B each represent a hydrogen atom, $R^1$ has the meanings given for $R^1$ hereinbefore with the exception of the hydrogen atom, the methyl group, ethyl group, allyl group and benzyl group, and $R^2$, $R^3$ and X are defined as hereinbefore.

Particularly preferred compounds of formula I mentioned hereinbefore are those wherein A and B each represent a hydrogen atom or together represent another carbon-carbon bond, $R^1$ represents a hydrogen atom, an alkyl group with 1 to 4 carbon atoms or an ethyl group substituted in the 2-position by a hydroxy, methoxy or methyl- mercapto group, $R^2$ represents a hydrogen atom or a methyl group and $R^3$ represents a hydrogen atom or $R^2$ represents a hydrogen atom and $R^3$ represents a methyl or ethyl group and X represents a methylene group, whilst the new quinolin-2,5-diones are those wherein, when A and B together represent another carbon- carbon bond, $R^2$ represents a methyl group and $R^3$ represents a hydrogen atom and $R^1$ and X are defined as hereinbefore or $R^1$ has the meanings given for $R^1$ hereinbefore with the exception of the hydrogen atom, the methyl and ethyl groups, and $R^2$, $R^3$ and X are defined as hereinbefore or, if A and B each represent a hydrogen atom and $R^1$ has the meanings given for $R^1$ hereinbefore with the exception of the hydrogen atom, the methyl and ethyl groups, and $R^2$, $R^3$ and X are defined as hereinbefore.

The above-mentioned new quinolin-2,5-diones are obtained according to the invention by the following processes:

a) reaction of a compound of formula

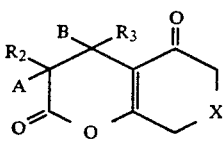

(II)

wherein

A, B, $R^2$, $R^3$ and X are as hereinbefore defined, with an amine of formula

(III)

wherein $R^1$ is defined as hereinbefore.

The reaction is preferably carried out in a solvent such as methanol, ethanol, isopropanol, tetrahydrofuran, dioxan, methylene chloride or benzene or in an excess of the amine of formula III used as solvent, conveniently at temperatures of between $-30°$ and 180° C., but preferably at temperatures between 15° and 50° C. The reaction may, however, also be carried out without a solvent.

b) Reaction of a compound of formula

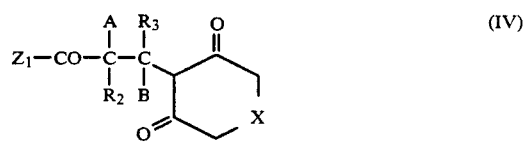

(IV)

(wherein

A, B, $R^2$, $R^3$ and X are defined as hereinbefore and $Z^1$ represents a nucleophilic leaving group such as a hydroxy group, an alkoxy group with 1 to 3 carbon atoms or a halogen atom) with an amine of formula

(III)

wherein $R^1$ is defined as hereinbefore.

The reaction is preferably carried out in a solvent such as methanol, ethanol, isopropanol, tetrahydrofuran, dioxan, methylene chloride or benzene or in an excess of the amine of formula III used as solvent, conveniently at temperatures of between $-30°$ and 200° C., but preferably at temperatures of between 140° and 180° C. The reaction may, however, also be carried out without a solvent.

c) In order to prepare compounds of formula I wherein $R^2$ represents a hydrogen atom:

Decarboxylation of a compound of formula

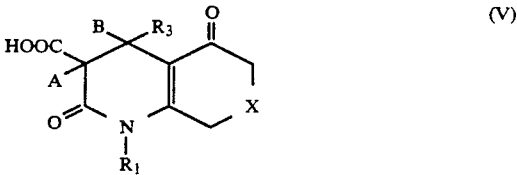

(V)

wherein

A, B, $R^1$, $R^3$ and X are defined as hereinbefore.

The decarboxylation is preferably carried out in a high-boiling solvent such as quinoline, collidine, dimethylsulphoxide, diphenyl, tetralin, decalin, o-dichlorobenzene, ethylene glycol or 2-n-butoxy- ethanol and optionally in the presence of a reaction accelerator such as copper powder at elevated temperatures, e.g. at temperatures above 80° C., but preferably at temperatures between 100° and 200° C. The reaction may, however, also be carried out without a solvent.

However, it is particularly advantageous to perform the reaction by preparing a compound of general formula V in the reaction mixture, for example by heating a corresponding ester such as the methyl, ethyl or isopropyl ester in a suitable solvent such as dimethylsulphoxide in the presence of an alkali metal halide, preferably lithium chloride or sodium chloride, and in the presence of water. The quantity of water required is conveniently 2 to 6 times the equimolar amount, preferably 3 to 4 times the equimolar amount, based on the ester used.

A compound of formula V used may also be prepared in the reaction mixture.

d) In order to prepare compounds of formula I wherein $R^1$ has the meanings given hereinbefore with the exception of a hydrogen atom:

reaction of a compound of formula

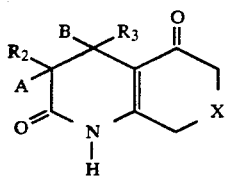
(VI)

wherein

A, B, $R^2$, $R^3$ and X are defined as hereinbefore, with a compound of formula $$Y-R^{1'} \quad (VII)$$

wherein $R^{1'}$ has the meanings given for $R^1$ hereinbefore with the exception of the hydrogen atom and Y represents a nucleophilic leaving group such as a halogen atom, e.g. a chlorine, bromine or iodine atom, or a sulphonyloxy group, e.g. a methane- sulphonyloxy or p-toluenesulphonyloxy group, or Y together with a beta-hydrogen atom of an alkyl group with 2 to 6 carbon atoms of the group $R^{1'}$ represents an oxygen atom.

The alkylation is carried out in a suitable solvent such as methanol, ethanol, diethylether, acetone, methylene chloride, tetrahydrofuran, dioxan, dimethyl- formamide or dimethylsulphoxide, but preferably in an aprotic solvent such as acetone, dimethylformamide or dimethylsulphoxide, in the presence of an inorganic base such as potassium carbonate, sodium hydroxide, sodium hydride or potassium hydroxide with a suitable alkylating agent such as methyl iodide, dimethyl sulphate, ethyl bromide, diethyl sulphate, benzyl chloride, n-propyl bromide, isopropyl bromide, 2-hydroxy-ethyl bromide, ethylene oxide or n-propylen- 2,3-oxide at temperatures of between 0° and 100° C., but preferably at temperatures of between 10° and 50° C.

e) In order to prepare compounds of formula I wherein A and B each represent a hydrogen atom:

reaction of an enaminoketone of formula

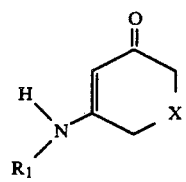
(VIII)

wherein $R^1$ and X are defined as hereinbefore, with a compound of formula

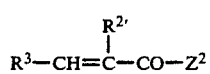
(IX)

wherein $R^2$ and $R^3$ are as hereinbefore defined and $Z^2$ represents a nucleophilic leaving group such as a hydroxy group, an alkoxy group with 1 to 3 carbon atoms or a halogen atom.

The reaction is conveniently carried out in a high boiling solvent such as tetralin, decalin, diphenyl or o-dichlorobenzene, but preferably without a solvent at elevated temperatures, e.g. at temperatures between 100° and 250° C., but preferably at temperatures between 120° and 180° C. However, it is particularly advantageous to carry out the reaction in a pressurised vessel.

As already mentioned hereinbefore, the new compounds may occur in the form of their enantiomers, mixtures of enantiomers or racemates or, if they contain 2 asymmetric carbon atoms, in the form of their diastereoisomers or mixtures of diastereoisomers.

Thus, the compounds of general formula I which contain only one optically active centre may be resolved into their optical antipodes by methods known per se (see Allinger N. L. and Eliel W. L. in "Topics in Stereochemistry", Vol. 6, Wiley Inter- science, 1971), e.g. by recrystallisation from an optically active solvent.

Moreover, the compounds of general formula I obtained having 2 asymmetric carbon atoms may be separated into their diastereoisomers on the basis of their physico-chemical differences using methods known per se, e.g. chromatography and/or fractional crystallisation. A pair of enantiomers thus obtained can then be resolved into the optical antipodes thereof, as described above.

The compounds of formulae II to IX used as starting materials are obtained by methods known from the literature.

Thus, a compound of formula II or IV is obtained by reacting a corresponding cyclohexan-1,3-dione with a corresponding carboxylic acid derivative, a compound of formula V which may be new is obtained by reacting a corresponding 2-amino-methylene-cyclohexan- 1,3-dione with a cyanoacetate and subsequent saponification or by reacting a corresponding cyclohexan-1,3-dione with an alkoxymethylenecyanoacetate and subsequent saponification and a compound of formula VI is obtained by cyclisation of a corresponding 1-aminocyclohexen-3-one with a corresponding alpha, beta-unsaturated carboxylic acid derivative.

A stereoselective starting compound of formula V which contains only one optically active centre in the 4-position can be prepared analogously to the method described by Enders et al. in Tetrahedron Letters 28, 3795-3798 (1987). In order to do this, for example (S)-1- amino-2-methoxymethyl-pyrrolidine is converted with dimedon or cyclohexan-1,3-dione into the corresponding (S)-hydrazone derivative which is then reacted, after metallisation, e.g. with n-butyllithium at −78° C., with a corresponding benzylidene-malonate. The resulting (S—R)-2-[(2-bis(alkoxycarbonyl)-1-phenyl)-ethyl]-3-[(2-methoxymethyl)-pyrrolidine-1-yl]-en-amino-cyclohexan-3-one is cyclised to form the corresponding quinolinedione, which is converted by acidic reduction, e.g. with zinc/glacial acetic acid, and simultaneous saponification into the desired compound of formula V, which is not isolated.

A further aspect of the present invention is the new quinolinediones of formula

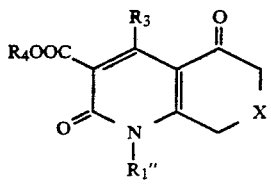

wherein $R^3$ and X are as hereinbefore defined, and $R^{1'''}$ represents a hydrogen atom, an alkyl group with 1 to 3 carbon atoms optionally substituted by a phenyl, fluorophenyl, chlorophenyl or bromophenyl group, by a carboxy group or by an alkoxycarboxyl group with 2 to 4 carbon atoms in all, an alkyl group with 4 to 6 carbon atoms, a cycloalkyl group with 3 to 6 carbon atoms, an alkenyl or alkynyl group with 3 to 5 carbon atoms, an alkyl group with 2 or 3 carbon atoms substituted in the 2- or 3-position by a hydroxy, alkoxy or alkylmercapto group, in which the alkoxy or alkylmercapto or alkylmercapto substituent may in each case contain 1 to 3 carbon atoms, or a tetrahydrofurfuryl group and $R^4$ represents an alkyl group with 1 to 5 carbon atoms, or $R^{1''}$ has the meanings given for $R^{1'''}$ above with the exception of a hydrogen atom and $R^4$ represents a hydrogen atom which can be converted directly or after conversion into the corresponding carboxylic acid into a corresponding compound of formula I in which $R^{1'''}$, $R^3$ and X are as hereinbefore defined.

According to the invention the new compounds are obtained by reaction of a cyclohexan -1,3-dione of formula

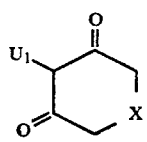

in which X is as defined hereinbefore, with a cyanoacetate of formula

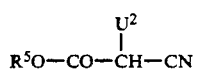

wherein

U1 represents a hydrogen atom and U2 together with the hydrogen atom of the neighbouring CH group represents a group of formula

or

U1 together with the hydrogen atom of the neighbouring CH group represents a group of formula

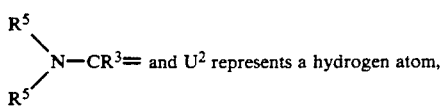

where $R^3$ is as hereinbefore defined and each $R^5$, which can be identical or different represents an alkyl group with 1 to 5 carbon atoms; reaction of the resulting tetrahydrocumarinone of formula

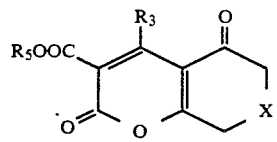

wherein $R^3$ and X are as hereinbefore defined and $R^5$ is as defined above, with an amine of formula

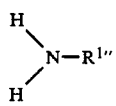

wherein $R^{1'''}$ is as defined above and, if desired, subsequent hydrolysis of an ester so obtained.

The cyclisation reaction is preferably effected in a solvent such as dimethylformamide, dimethylsulphoxide, dioxan or chloroform, optionally in the presence of a base such as sodium ethoxide, potassium hydroxide, potassium tertbutoxide or sodium hydride, at temperatures between −20° and +50° C., but preferably at ambient temperature.

The subsequent reaction with an amine of formula III is expediently effected in a solvent such as ethanol, dimethylformamide, dimethylsulphoxide, dioxan, chloroform or also in the amine of formula III itself as solvent, at temperatures between 0° and 50° C., preferably at ambient temperature.

The subsequent hydrolysis, whereby a product of formula V or X is obtained, is preferably effected in an aqueous solvent such as ethanol/water, dioxan/water or water, and preferably in the presence of an acid such as hydrochloric or sulphuric acid or in the presence of a base such as sodium hydroxide or potassium hydroxide at elevated temperatures, preferably at the boiling temperature of the reaction mixture.

A compound of formula Ia can particularly advantageously be obtained as characterised in claim 18 from a compound of formula X thus obtained, according to the process c) as described previously.

As already mentioned hereinbefore, the compounds of general formula I have valuable pharmacological properties, particularly antipyretic, analgesic and/or antiphlogistic properties.

For example, the following compounds:
A = 1-methyl-7,8-dihydro-2,5(1H,6H)-quinolinedione,
B = 3-methyl-3,4,7,8-tetrahydro-2,5(1H,6H)-quinolinedione,
C = 1-methyl-3,4,7,8-tetrahydro-2,5(1H,6H)-quinolinedione,
D = 4-methyl-7,8-dihydro-2,5(1H,6H)-quinolinedione,
E = 3-methyl-7,8-dihydro-2,5(1H,6H)-quinolinedione,
F = 1,3-dimethyl-7,8-dihydro-2,5(1H,6H)-quinolinedione,
G = 1-ethyl-4-methyl-7,8-dihydro-2,5(1H,6H)-quinolinedione,
H = 1-n-butyl-4-methyl-7,8-dihydro-2,5(1H,6H)-quinolinedione and
I = 1-ethyl-3,4,7,8-tetrahydro-2,5(1H,6H)-quinolinedione
were tested as follows:

1. The effect on the pain of inflammation in rats was tested using the method of RANDALL and SELITTO (Arch. int. Pharmacodyn. 111, 409 (1957)). The test substances were administered to male rats weighing between 100 and 130 g as a trituration in 1% methylcellulose (1.0 ml/100 g of animal) 90 or 135 minutes after subcutaneous administration of yeast by oesophageal tube. From the pain threshold measured 90 or 45 minutes after administration of the various doses, the $ED^{50}$ was determined by linear regression analysis as the dosage which raised the pain threshold by 50%. The following Table contains the results obtained:

| Substance | $ED^{50}$ mg/kg | |
|---|---|---|
| | after 45 minutes | after 90 minutes |
| A | 8.7 | 8.1 |
| B | 37.0 | 39.0 |
| C | 15.0 | 21.0 |
| D | 21.0 | 34.0 |
| E | 31.0 | 36.0 |
| F | 12.5 | 12.1 |
| G | 5.1 | 5.9 |
| H | | 19.1 |
| I | 13.0 | 16.0 |

2. The effect on heat-induced pain in mice was investigated using the method of CHEN and BECKMAN (Science 113, 631 (1951)). Male mice with an average weight of 20 g were given the test substances as a trituration in 1% methylcellulose (0.1 ml/10 g of animal by oesophageal tube. From the lengthening of the individual reaction time observed after various doses, the $ED^{100}$ was calculated by linear regression analysis as the dosage which doubled the reaction time.

The Table which follows contains the results obtained:

| SUBSTANCE | $ED^{100}$ mg/kg |
|---|---|
| A | 71 |
| B | 155 |
| C | 99 |
| D | 98 |
| E | 135 |
| F | 109 |
| G | 59 |
| H | 101 |
| I | 70 |

3. The effect on mechanically induced pain was investigated by the tail clamp method according to HAFFNER (Dtch. med. Wschr. 54, 731 (1929)). Male mice weighing between 19 and 24 g were given the test substances as a trituration in 1% methyl- cellulose (0.1 ml/10 g of animal) by oesophageal tube. At intervals of 30 minutes, the number of mice which no longer reacted to the putting on of the clamp was determined after the treatment.

An $ED^{50}$ was calculated by probit analysis from the percentage of animals which showed no pain-reaction after various doses.

The following Table contains the results obtained:

| Substance | $ED^{50}$ mg/kg |
|---|---|
| A | 80 |
| B | 100 |
| C | 129 |
| D | 129 |
| E | 102 |
| F | 86 |
| G | 26 |
| H | 50 |
| I | 55 |

4. The effect on body temperature was investigated on normothermic rats weighing between 120 and 140 g. The test substances were administered by oesophageal tube as a trituration in 1% methylcellulose (1.0 ml/100 g of animal). From the lowering of rectal temperature observed after various dosages, the $ED^{-1.5°\ C.}$ was calculated by linear regression analysis as the dosage which lowered the body temperature by 1.5° C.

The following Table shows the results obtained:

| Substance | $ED^{-1.5°\ C.}$ mg/kg |
|---|---|
| A | 29 |
| B | 35 |
| C | 26 |
| D | 25 |
| E | 34 |
| F | 36 |
| G | 11 |
| H | 36 |
| I | 22 |

5. The acute toxicity was determined in mice or rats of both sexes with an average weight of 20 g. The test substances were administered by oesophageal tube as a trituration in 1% methylcellulose (0.2 ml/10 g of animal). Wherever possible the LD50 was calculated according to LITCHFIELD and WILCOXON (J. Pharmacol. exp. Therap. 96, 99 (1949)) from the percentage of animals which died within 14 days after receiving various doses.

The following Table shows the results obtained:

| Substance | $LD^{50}$ mg/kg | |
|---|---|---|
| | Mouse | Rat |
| A | 767 | 489 |
| B | 1220 | 659 |
| C | 985 | 748 |
| D | — | 1370 |
| E | 825 | |
| F | 296 | 396 |
| G | — | — |
| H | — | — |
| I | — | — |

The pharmacological properties found show that the compounds of general formula I are analgesics/antipyretics of the same type as aminophenazone. They are therefore suitable for combatting pain such as headache, toothache, menstrual pain, neuralgia, migraine, post-operative and post-traumatic pain, and also for combatting fever and inflammation or cold symptoms. The compounds of general formula I, optionally combined with other active substances, may be formulated with one or more inert carriers and/or diluents, e.g. with water, corn starch, potato starch, lactose, glucose, microcrystalline cellulose, magnesium stearate, polyvinylpyrrolidone, hard fat, carboxymethylcellulose or suitable mixtures thereof, to produce conventional galenic preparations such as plain or coated tablets, capsules, powders, suppositories, suspensions and solutions. The single dose in adults is 25–1200 mg, conveniently 50–600 mg, but preferably 100 to 300 mg.

The Examples which follow are intended to illustrate the invention:

EXAMPLE A 7,8-Dihydro-2,5(1H,6H)-quinolinedione 3-carboxylate 45.0 g (0.269 mol) of 2-dimethylaminomethylene-cyclohexan-1,3-dione and 43 ml (1.5×0.269 mol) of ethyl cyanoacetate are refluxed for 1.5 hours in 400 ml of absolute ethanol. After cooling, the light yellow crystals precipitated are suction filtered, washed with a little cold ethanol and dried. Melting point: 227°–233.5° C., Yield: 60.8 g (96.1% of theory).

b)
7,8-Dihydro-2,5(1H,6H)-quinolinedione-3-carboxylic acid 50.0 g of ethyl 7,8-dihydro-2,5(1H,6H)-quinolinedione- 3-carboxylate are stirred with 1000 ml of semiconcentrated hydrochloric acid for 16 hours. The crystalline precipitate formed is suction filtered, washed with a little water and dried at 70° C. Melting point: 250° C., Yield: 33.9 g (77.7% of theory).

c) 7,8-Dihydro-2,5(1H,6H)-quinolinedione 36.5 g (0.1762 mol) of 7,8-dihydro-2,5(1H,6H)-quinolinedione-3-carboxylic acid are heated together with 4.0 g of copper powder in 330 ml of quinoline under nitrogen in an oil bath at 230° C. As soon as the internal temperature exceeds 160° C. gas begins to develop, slowly at first and then more vigorously, the development of gas dies away again after 30 minutes and after 40 minutes it has ceased. The copper powder is then left to stand, the supernatant solution still at 160° C. is decanted off and then stirred with further cooling, finally in an ice bath, whereupon crystallisation occurs. The crude product is suction filtered and recrystallised from 400 ml of ethanol/water (7:3) with the addition of activated charcoal. Melting point: 302°–303° C., Yield: 16.6 g (57.6% of theory).

EXAMPLE B

1-Methyl-7,8-dihydro-2,5(1H,6H)-quinolinedione 3.36 g (0.0206 mol) of 7,8-dihydro-2,5(1H,6H)-quinolinedione are stirred with 5.69 g (2×0.0206 mol) of powdered anhydrous potassium carbonate and 1.92 ml (1.5×0.0206 mol) of methyl iodide in 35 ml of dimethylformamide for 16 hours at ambient temperature. The mixture is then suction filtered, the solvent is evaporated off in vacuo and the residue is recrystallised from chloroform/ethyl acetate. Melting point: 203°–205° C., Yield: 3.1 g (84.9% of theory).

EXAMPLE C

4-Methyl-7,8-dihydro-2,5(1H,6H)-quinolinedione a) 4-Methyl-5,6,7,8-tetrahydro-cumarin-5-one 231.2 g (2.0 mol) of cyclohexan-1,3-dione (97%) are refluxed under nitrogen for 2.5 hours in 670 ml of absolute pyridine with 325.3 q (1.25×2.0 mol) of ethyl acetoacetate and 4.88 (0.02×2 mol) of 4-dimethylaminopyridine. Then 65.1 g (0.25×2.0 mol) of ethyl acetoacetate are again added and the mixture is boiled for a further 3 hours. The pyridine is then distilled off in vacuo and the oily residue is stirred while still warm with 100 ml of a mixture of cyclohexane/ethyl acetate (1:1). The reaction product which crystallises out is suction filtered and dried. Yield: 136.9 g (39.2% of theory) The mother liquor is freed from solvent in vacuo using a rotary evaporator and the oily residue is distilled in vacuo. The distillate solidifies into a white crystalline substance.

Bp0.1–0.15 = 190°–210° C.
Yield: 126 g (35.4% of theory),
Total yield: 265.6 g (74.5% of theory).
Melting point: 96°–97° C. (after column chromatography on silica gel using ethyl acetate/methylene chloride (1:1)).

The following compound is prepared analogously:
4-ethyl-5,6,7,8-tetrahydro-cumarin-5-one
Melting point: 54°–55° C.

b) 4-Methyl-7,8-dihydro-2,5(1H,6H)-quinolinedione 4.46 g (0.025 mol) of 4-methyl-5,6,7,8-tetrahydro-cumarin-5-one are heated to 180° C. for 3 hours in 150 ml of saturated methanolic ammonia in a stirred autoclave. After cooling, the methanolic ammonia is distilled off using a rotary evaporator and the residue is recrystallised from ethanol using activated charcoal.

Melting point: 278°–280° C.,
Yield: 4.01 g (64.7% of theory).

EXAMPLE D 1,4-Dimethyl-7,8-dihydro-2,5(1H,6H)-quinolinedione 4.46 g (0.025 mol) of 4-methyl-5,6,7,8-tetrahydro-cumarin-5-one are dissolved in a mixture of 41.9 g of liquid methylamine in 100 ml of methanol pre-cooled to −9° C., With cooling, and heated to 180° C. for 3 hours in an autoclave. After cooling the methanol and methylamine are distilled off using a rotary evaporator, the residue is chromatographed on a silica gel column using ethylene chloride/ethanol (95:5) and recrystallised from cyclohexane/ethyl acetate (1:1).

Melting point: 120°–121.5° C.,
Yield: 3.77 g (78.9% of theory).

EXAMPLE E

3-Methyl-7,7-dimethyl-3,4,7,8-tetrahydro-2,5(1H,6H)-quinolinedione

Prepared analogously to Example G from 1-amino-5,5-dimethylcyclohexen-3-one and methacrylic acid in an autoclave at 180° C. over a period of one hour.

Melting point: 198°–200° C.,
Yield: 28.9% of theory.

EXAMPLE F

4,7,7-Trimethyl-7,8-dihydro-2,5(1H,6H)-quinolinedione

Prepared from 4,7,7-trimethyl-5,6,7,8-tetrahydrocumarin-5-one and methanolic ammonia analogously to Example C(b).

Melting point: 305°–307° C.,
Yield: 56.0% of theory.

EXAMPLE G

3,4,7,8-Tetrahydro-2,5(1H,6H)-quinolinedione 5.00 g (0.675 mol) of 1-amino-cyclohexen-3-one and 65.65 g (1.35×0.675 mol) of acrylic acid are stirred for 3 hours under nitrogen in an oil bath heated to 180° C. The mixture is cooled and recrystallised from 1000 ml of methanol.

Melting point: 192°–194.5° C.,
Yield: 45.1% of theory,

EXAMPLE H

1-Methyl-3,4,7,8,7-tetrahydro-2,5(1H.6H)-quinolinedione

Prepared from 3,4,7,8-tetrahydro-2,5(1H,6H)-quinoline- dione and methyl iodide using potassium carbonate in acetone.

Melting point: 72°–74° C.,
Yield: 82.9% of theory.

EXAMPLE I

1-benzyl-3,4,7,8-tetrahydro-2,5(1H,6H)-quinolinedione

Prepared analogously to Example H from 3,4,7,8-tetrahydro-2,5(1H,6H)-quinolinedione and benzyl bromide.

Melting point: 63.5°–65° C.,
Yield: 98.4% of theory.

EXAMPLE K

3-Methyl-3,4,7,8-tetrahydro-2,5(1H,6H)-quinolinedione

Prepared analogously to Example G from 1-amino-cyclohexen-3-one and methacrylic acid in an autoclave for a period of one hour at 180° C. Recrystallisation is from methanol and subsequently from a mixture of ethyl acetate/ethanol (3:1).

Melting point: 210°–212° C.,
Yield: 28.8% of theory.

EXAMPLE L

7,7-Dimethyl-3,4,7,8-tetrahydro-2,5(1H,6H)-quinolinedione

Prepared analogously to Example G from 1-amino-5,5-dimethyl-cyclohexen-3-one and acrylic acid at 140° C. for 3 hours.

Melting point: 161°–65.5° C.,
Yield: 95% of theory.

EXAMPLE M b 1-Methyl-7,8-dihydro-2,5(1H,6H)-quinolinedione a) Ethyl 7,8-dihydro-5-oxo(6H)cumarin-3-carboxylate 33.6 g (0.3 mol) of 97% 1,3-cyclohexanedione are dissolved in 500 ml of dimethylformamide and 33.7 g (0.3 mol) of potassium tert.butoxide are added whilst cooling with ice. Then 50.75 g (0.3 mol) of ethyl ethoxymethylenecyanoacetate dissolved in 100 ml of dimethylformamide are added within 20 minutes, the temperature being maintained at between 15 and 20° C. This solution is stirred overnight at ambient temperature, then added to a mixture of 750 g of ice and 320 ml of 2N hydrochloric acid and stirred for 20 minutes. Finally, it is extracted 5 times with 100 ml of ethyl acetate. The organic phases are washed 5 times with saturated sodium chloride solution and then concentrated by evaporation.

Yield: 65.9 g (93% of theory).

The following compounds may be prepared analogously:

ethyl 7,8-dihydro-7-methyl-5-oxo(6H)cumarin-3-carboxylate ethyl 7,8-dihydro-7,7-dimethyl-5-oxo(6H)cumarin-3carboxylate [Melting point: 93–95° C.]

b) Ethyl 1-methyl-7,8-dihydro-2,5(1H,6H)-quinolinedione-3-carboxylate 40.58 g (0.17 mol) of ethyl 7,8-dihydro-5-oxo-(5H)-cumarin-3-carboxylate are dissolved in 200 ml of ethanol and at ambient temperature one equivalent of a 5 molar ethanolic methylamine solution is added dropwise. A precipitate is formed, which is stirred for a further 2 hours at ambient temperature. The reaction mixture is evaporated down to 150 ml and cooled in an ice bath. The precipitate is suction filtered and washed twice with cold ethanol.

Melting point: 140°–142° C.,
Yield: 35 g (81% of theory).

c) 1-Methyl-7,8-dihydro-2,5(1H,6H)-quinolinedione 29.1 g (0.5 mol) of finely powdered lithium chloride are suspended in 3.5 ml of water and 50 ml of dimethylsulphoxide and 12.1 q (o.05 mol) of ethyl 1-methyl-7,8-dihydro-2,5(1H,6H)-quinolinedione-3-carboxylate are added in batches thereto. The reaction mixture is stirred for 6 hours in a hot oil bath at 190° C. After the development of carbon dioxide has ceased, the suspension is poured onto 300 g of ice. The solution is then extracted with 5 times 100 ml of chloroform. The organic phases are washed with 3 times 50 ml of saturated sodium chloride solution, dried over sodium sulphate and concentrated by rotary evaporation.

Melting point: 205°–208° C. (ethanol),
Yield: 5.9 g (67.3% of theory).

The following compounds may be prepared analogously to Example M:

1-ethyl-7,8-dihydro-2,5(1H,6H)-quinolinedione [Melting point: 149°–150° C.]

1-methyl-7-methyl-7,8-dihydro-2,5(1H,6H)-quinolinedione 1-methyl-7,7-dimethyl-7,8-dihydro-2,5(1H,6H)-quinolinedione [Melting point: 130°–131° C.]

EXAMPLE 1

1-Phenyl-7,8-dihydro-2,5(1H,6H)-quinolinedione a) Ethyl 1-phenyl-7,8-dihydro-2,5(1H,6H)-quinolinedione-3-carboxylate 43 g (0.2 mol) of 2-phenylaminomethylene-cyclohexan- 1,3dione are dissolved at 80° C. in 150 ml of dry dimethylformamide. 29.2 g of ethyl cyanoacetate are added and then, within 10 minutes, a solution of 20 g (1.78×0.2 mol) of potassium hydroxide in 200 ml of absolute ethanol is added dropwise thereto. The reaction mixture heats up until it begins to boil. It is then stirred for 5 minutes at 80° C., cooled to 15° C., poured into 1000 ml of water and adjusted to pH 1.0 with concentrated hydrochloric acid. After standing overnight, pink crystals are formed which are suction filtered and dried.

Melting point: 254° C. (decomp.)
Yield: 36.9 g (59.3% of theory).

b) 1-Phenyl-7,8-dihydro-2,5(1H,6H)-quinolinedione-3-carboxylic acid 61.7 g (0.2 mol) of ethyl 1-phenyl-7,8-dihydro-2,5(1H,6H)-quinolinedione-3-carboxylate are stirred in 750 ml of 6N hydrochloric acid for 48 hours at ambient temperature. The white crystals are separated by suction filtering from the slightly fluorescent solution and dried.

Melting point: greater than 270° C.,
Yield: 52.2 g (92.1% of theory).

c) 1-Phenyl-7,8-dihydro-2,5(1H,6H)-quinolinedione 33.0 g (0.12 mol) of 1-phenyl-7,8-dihydro-2,5(1H,6H)-quinolinedione-3-carboxylic acid are decarboxylated analogously to Example A(c) in quinoline at 140° C. with the addition of a trace of copper powder. 800 ml of petroleum ether are added to the reaction mixture and the greyish-brown reaction product precipitated is suction filtered. It is chromatographed on a silica gel column using ethyl acetate as eluant.

Melting point: 147°-149.2° C.,
Yield: 21.3 g (76.6% of theory).

EXAMPLE 2

1-(4-Chlorophenyl)-7,8-dihydro-2,5(1H,6H)-quinolinedione

Prepared analogously to Example 1 starting from 2-(4-chlorophenyl) -aminomethylene-cyclohexan-1,3-dione, saponification and decarboxylation of the resulting ethyl 1-( 4-chlorophenyl)-7,8-dihydro- 2,5(1H,6H)-quinolinedione-3carboxylate.

Melting point: 196°-199.5° C.,
Yield: 60.4% of theory.

EXAMPLE 3

1-(4-Methyl-phenyl)-7,8-dihydro-2,5(1H,6H)-quinolinedione

Prepared analogously to Example 1 starting from 2-(4-methyl-phenyl) -aminomethylene-cyclohexan-1,3-dione, with subsequent saponification and decarboxylation of the resulting ethyl 1-(4-methyl-phenyl)-7,8-dihydro- 2,5(1H,6H)-quinolinedione-3-carboxylate.

Melting point: 192°-194° C.,
Yield: 53.3% of theory.

EXAMPLE 4

1-(4-Methoxyphenyl)-7,8-dihydro-2,5(1H,6H)-quinolinedione

Prepared analogously to Example 1 starting from 2-(4-methoxy-phenyl) -aminomethylene-cyclohexan-1,3-dione, with subsequent saponification and decarboxylation of the resulting ethyl 1-(4-methoxy-phenyl)-7,8-dihydro-2,5(1H,6H)-quinolinedione-3-carboxylate.

Melting point: 164°-166° C.,
Yield: 28.6% of theory,

EXAMPLE 5

3-Methyl-7,8-dihydro-2,5(1H,6H)-quinolinedione a) 3-Methyl-5,6,7,8-tetrahydro-cumarin-5-one Prepared analogously to Example C(a) from cyclohexan- 1,3-dione and ethyl 2-formyl-propionate.
Melting point: 83°-86° C.,
Yield: 75.7% of theory.

b) 3-Methyl-7,8-dihydro-2,5(1H,6H)-quinolinedione 3.0 g (0.0168 mol) of 3-methyl-5,6,7,8-tetrahydro-cumarin-b 5-one are dissolved in 50 ml of saturated methanolic ammonia and left to stand for 2 days at ambient temperature. Then the shiny, platelet- shaped crystals precipitated are suction filtered, washed with a little cold methanol and dried.

Melting point: 287°-290° C. (decomp.),
Yield: 2.16 g (72.6% of theory).

EXAMPLE 6

1,3-Dimethyl-7,8-dihydro-2,5(1H,6H)-quinolinedione

Prepared analogously to Example 5(b) from 3-methyl- 5,6,7,8-tetrahydro-cumarin-5-one and methanolic methylamine solution a ambient temperature. After evaporation of the methanolic ammonia the residue is recrystallised from water with the addition of charcoal.

Melting point: 127°-129° C.,
Yield: 70.2% of theory.

EXAMPLE 7

1-Ethyl-3-methyl-7,8-dihydro-2,5(1H,6H)-quinolinedione

Prepared analogously to Example 5(b) from 3-methyl- 5,6,7,8-tetrahydro-cumarin-5-one and ethylamine.
Melting point: 155°-160° C.,
Yield: 81.9% of theory.

EXAMPLE 8

1-(2-Hydroxyethyl)-3-methyl-7,8-dihydro-2,5(1H.6H)-quinolinedione

Prepared analogously to Example 5(b) from 3-methyl- 5,6,7,8-tetrahydro-cumarin-5-one and 2-hydroxyethylamine.
Melting point: 146°-152° C.,
Yield: 88.4% of theory.

EXAMPLE 9

1-(2-Methylmercaoto-ethyl)-3-methyl-7,8-dihydro-2,5(1H,6H)-quinolinedione

Prepared analogously to Example 5(b) from 3-methyl- 5,6,7,8-tetrahydro-cumarin-5-one and 2-methylmercapto- ethylamine.
Melting point 86°-88.5° C.,
Yield: 53.1% of theory.

EXAMPLE 10

1-(2-Hydroxy-ethyl)-4-methyl-7,8-dihydro-2,5(1H 6H)-quinolinedione

Prepared analogously to Example 5(b) from 4-methyl- 5,6,7,8-tetrahydro-cumarin-5-one and 2-hydroxyethylamine.
Melting point: 111°-112° C.,
Yield: 91.6% of theory.

EXAMPLE 11

1-(2-Methoxy-ethyl)-4-methyl-7,8-dihydro-2,5,(1H,6H)-quinolinedione

Prepared analogously to Example 5(b) from 4-methyl- 5,6,7,8-tetrahydro-cumarin-5-one and 2-methoxy-ethylamine.
Melting point: 105°-107° C.,
Yield: 83.7% of theory.

EXAMPLE 12

1-Isopropyl-4-methyl-7,8-dihydro-2,5(1H,6H)-quinolinedione

Prepared analogously to Example 5(b) from 4-methyl- 5,6,7,8-tetrahydro-cumarin-5-one and isopropylamine.
Melting point: 89.5°-90.5° C.,
Yield: 16.8% of theory.

EXAMPLE 13

1-n-Butyl-4-methyl-7,8-dihydro-2,5(1H,6H)-quinolinedione

Prepared analogously to Example 5(b) from 4-methyl- 5,6,7,8-tetrahydro-cumarin-5-one and n-butylamine.
Melting point: 58.5°-60° C.,
Yield: 86.1% of theory.

EXAMPLE 14

1-Methyl-4-trifluoromethyl-7,8-dihydro-2,5(1H,6H)-quinolinedione a) 4-Trifluoromethyl-5,6,7,8-tetrahydro-cumarin-5-one Prepared analogously to Example C(a) from cyclohexan- 1,3dione and ethyl omega,omega,omega-trifluoroacetoacetate.
Melting point: 78°-80° C.,
Yield: 10.1% of theory.

b)
1-Methyl-4-trifluoromethyl-7,8-dihydro-2,5(1H,6H)-quinolinedione

Prepared analogously to Example 5(b) from 4-trifluoro-methyl-5,6,7,8-tetrahydro-cumarin-5-one and methylamine at ambient temperature.
Melting point: 98°-99° C.,
Yield: 8% of theory.

EXAMPLE 15

4-Ethyl-7,8-dihydro-2,5(1H,6H)-quinolinedione

Prepared from 4-ethyl-5,6,7,8-tetrahydro-cumarin-5-one (prepared from ethyl 3-oxo-n-valeriate and cyclohexan-1,3dione) and methanolic ammonia in an autoclave for 1 hour at 140° C.
Melting point: 218°-220° C.,
Yield: 62.0% of theory.

EXAMPLE 16

1-Methyl-4-ethyl-7,8-dihydro-2,5(1H.6H)-quinolinedione

Prepared from 4-ethyl-5,6,7,8-tetrahydro-cumarin-5-one and methanolic methylamine solution over 31 hours at ambient temperature.
Melting point: 102°-103° C.,
Yield: 78% of theory.

EXAMPLE 17

3,4-Dimethyl-7,8-dihydro-2,5(1H,6H)-quinolinedione

Prepared from 3,4-dimethyl-5,6,7,8-tetrahydro-cumarin- 5-one (melting point: 109°-111° C., prepared from methyl 2methylacetoacetate and cyclohexan-1,3-dione) and methanolic ammonia for one hour in an autoclave at 150° C.
Melting point: 274°-276° C.,
Yield: 72.0% of theory.

EXAMPLE 18

1,3,4-Trimethyl-7,8-dihydro-2,5(1H,6H)-quinolinedione

Prepared from 3,4-dimethyl-5,6,7,8-tetrahydro-cumarin- 5-one and methanolic methylamine solution over a period of 15 hours at ambient temperature.
Melting point: 197°-199° C.,
Yield: 98.6% of theory.

EXAMPLE 19

1-(2-Hydroxy-ethyl)-3,4-dimethyl-7,8-dihydro-2,5(1H.6H)-quinolinedione

Prepared from 3,4-dimethyl-5,6,7,8-tetrahydro-cumarin- 5-one and 2-hydroxy-ethylamine at 130° C. over a period of 25 minutes.
Melting point: 140°-141° C.,
Yield: 56.0% of theory.

EXAMPLE 20

2,3,6,7-Tetrahydro-4,9(1H,5H,8H)-cyclopenta[c]quinolinedione

Prepared from 2,3,6,7-tetrahydro-4,9(1H,8H)-cyclopenta-[c][1]benzopyrandione (prepared from cyclohexan- 1,3-dione and ethyl cyclopentanone-2-carboxylate) with methanolic ammonia over a period of one hour at 140° C. in an autoclave.
Melting point: 305°-312° C.,
Yield: 91.2% of theory.

EXAMPLE 21

Methyl-2,3,6,7-tetrahydro-4,9(aH,5H,8H)-cyclopenta[c]-quinolinedione

Prepared from 2,3,6,7-tetrahydro-4,9(1H,8H)-cyclopenta-[c][1]benzopyrandione and methylamine at ambient temperature over a period of one and a half hours.
Melting point 224°-226° C.,
Yield: 92.1% of theory.

EXAMPLE 22

5-(2-Hydroxy-ethyl)-2,3,6,7-tetrahydro-4,9(1H,5H,8H)-cyclopenta[c]quinolinedione Prepared from 2,3,6,7-tetrahydro-4,9(1H,8H)-cyclopenta-[c][1]benzopyrandione and 2-hydroxy-ethylamine.
Melting point: 162.5°-163.5° C.,
Yield: 81.1% of theory.

EXAMPLE 23

3,4,7,8,9,10-Hexahydro-1,6(2H,5H)-phenanthridinedione

Prepared from 3,4,7,8,9,10-hexahydro-1,6(2H)-dibenzo-[b,d]pyrane (prepared from cyclohexan-1,3-dione and ethyl cyclohexanone-2-carboxylate) with methanolic ammonia over a period of one hour in an autoclave at 140° C.
Melting point: 303°–306° C.,
Yield: 91.7% of theory.

EXAMPLE 24

5-(2-Hydroxy-ethyl)-3,4,7,8,9,10-hexahydro-1,6(2H,5H)-phenanthridinedione

Prepared from 3,4,7,8,9,10-hexahydro-1,6(2H)-dibenzo-[b,d]pyrane and 2-hydroxy-ethylamine at 125° C. for 55 minutes.
Melting point: 152°–153° C.,
Yield: 77.1% of theory.

EXAMPLE 25

4-Phenyl-7,8-dihydro-2,5(1H,6H)-quinolinedione

Prepared from 4-phenyl-5,6,7,8-tetrahydro-cumarin-5-one (melting point: 167°–168° C., prepared from ethyl benzoylacetate and cyclohexan-1,3-dione) and methanolic ammonia in an autoclave over a period of one hour at 135° C.
Melting point: 278°–281° C.,
Yield: 82.5% of theory.

EXAMPLE 26

1-Methyl-4-phenyl-7,8-dihydro-2,5(1H,6H)-quinolinedione

Prepared from 4-phenyl-5,6,7,8-tetrahydro-cumarin-5-one and methanolic methylamine at ambient temperature.
Melting point: 164°–165° C.,
Yield: 85.7% of theory.

EXAMPLE 27

1-Ethyl-3,4,7,8-tetrahydro-2,5(1H,6H)-quinolinedione 21.2 g (0.1 mol) of 2-(2-carbethoxy-ethyl)-cyclohexan-1,3-dione and 200 ml of 24% ethanolic ethylamine solution are heated to 180° C. in a stirred autoclave for 3 hours. The reaction solution is evaporated down using a rotary evaporator and the residue is chromatographed on a silica gel column with cyclohexane/ethyl acetate (1:1).
Melting point: 88°–92° C.
Yield: 11.6 g (60.0% of theory).

EXAMPLE 28

1-(2-Hydroxyethyl)-3,4,7,8-tetrahydro-2,5(1H,6H)-quinolinedione

Prepared analogously to Example 27 from 2-(2-carbethoxy-ethyl)-cyclohexan-1,3-dione and 2-hydroxy-ethylamine.
Melting point: 103°–104.5° C.,
Yield: 45% of theory.

EXAMPLE 29

1-Carbomethoxymethyl-3,4,7,8-tetrahydro-2,5(1H,6H)-quinolinedione 3.17 g (0.019 mol) of 3,4,7,8-tetrahydro-2,5(1H,6H)-quinolinedione are dissolved in 25 ml of dimethylformamide, mixed with 5.3 g (1.2×0.019 mol) of anhydrous. potassium carbonate and then with 3.52 g (2×0.019 mol) of methyl bromoacetate and the mixture is stirred for 16 hours at ambient temperature. The mixture is neutralised with methanolic hydrochloric acid and evaporated down in a rotary evaporator. The residue is purified by column chromatography (silica gel, eluant: cyclohexane/ethyl acetate (1:1)).
Melting point: 87°–89° C.,
Yield: 3.46 g (76% of theory).

EXAMPLE 30

1-(4-Chlorobenzyl)-3,4,7,8-tetrahydro-2,5(1H.6H)-quinolinedione

Prepared analogously to Example 29 from 3,4,7,8-tetrahydro-2,5(1H,6H)-quinolinedione and 4-chlorobenzyl- chloride.
Melting point: 100°–102° C.,
Yield: 55.4% of theory.

EXAMPLE 31

1-(2-Phenylethyl)-3,4,7,8-tetrahydro-2,5(1H,6H)-quinolinedione

Prepared analogously to Example 27 from 2-(2-carbethoxy-ethyl)-cyclohexan-1,3-dione and 2-phenylethylamine in boiling xylene using a water separator.
Melting point: 94.5°–97° C.,
Yield: 36.8% of theory.

EXAMPLE 32

1,3-Dimethy-3,4,7,8-tetrahydro-2,5(1H,6H)-quinolinedione

Prepared analogously to Example 29 from 3-methyl-3,4,7,8-tetrahydro-2,5(1H,6H)-quinolinedione and methyl iodide in boiling acetone.
Melting point: 63°–64° C.,
Yield: 84.5% of theory.

EXAMPLE 33

1-Ethyl-4-methyl-7 B-dihydro-2,5(1H,6H)-quinolinedione 12.5 g (0.07 mol) of 4-methyl-5,6,7,8-tetrahydrooumarin-5-one are dissolved in a 24% ethanolic ethylamine solution and left to stand at ambient temperature for 3 days. The mixture is then evaporated down and the residue is re-crystallised from ethyl acetate/cyclohexane.
Melting point: 97°–98° C.,
Yield: 13.3 g (92.6% of theory).
The following compounds are prepared analogously to Example 33:
1-propyl-4-methyl-7,8-dihydro-2,5(1H,6H)-quinolinedione Melting point: 108°–109° C.
1-isopropyl-4-methyl-7,8-dihydro-2,5(1H,6H)-quinolinedione Melting point: 89.5°–90.5° C.
4-ethyl-1-methyl-7,8-dihydro-2,5(1H,6H)-quinolinedione Melting point: 102°–103° C.
1,4-diethyl-7,8-dihydro-2,5(1H,6H)-quinolinedione [Melting point: 65°–70° C.].

EXAMPLE 34

1-(2-Methoxy-ethyl)-7,8-dihydro-2,5(1H,6H)-quinolinedione a) Ethyl 1-(2-methoxy-ethyl-7,8-dihydro-2,5(1H,6H)-quinolinedione-3-carboxylate 23.6 g (0.1 mol) of ethyl 7,8-dihydro-5-oxo-(5H)-cumarin-3-carboxylate are dissolved in 40 ml of ethanol and at ambient temperature 7.5 g (0.1 mol) of 2-methoxy-ethylamine dissolved in 20 ml of ethanol are added dropwise. A precipitate is formed which is stirred for another 2 hours at ambient temperature. The reaction mixture is evaporated down, the precipitate is removed by suction filtering, dissolved in 500 ml of ethyl acetate and filtered over a silica gel column.

Yield: 14.3 g of oil (48% of theory).

b)
1-(2-Methoxy-methyl)-7,8-dihydro-2,5(1H,6H)-quinolinedione 21.9 g (0.375 mol) of finely powdered sodium chloride are suspended in 2.7 ml of water and 60 ml of dimethylsulphoxide and 11.0 g (0.375 mol) of ethyl 1-(2-methoxy-methyl)-7,8-dihydro-2,5(1H,6H)-quinolinedione- 3-carboxylate are added in batches thereto. The reaction mixture is stirred for 6 hours in an oil bath at 190° C. After the development of carbon dioxide has ceased, the suspension is poured onto 300 g of ice. The solution is then extracted 3 times with 150 ml of chloroform. The organic phases are washed 5 times with 50 ml of saturated sodium chloride solution, dried over sodium sulphate and concentrated by rotary evaporation. Finally, the residue is chromatographed over a silica gel column (eluant: ethyl acetate/methanol=15/1).

Melting point: 119°-121° C.,
Yield: 3.0 g (36% of theory).

The following compounds are prepared analogously to Example 34:

1-(2-hydroxy-ethyl)-7,8-dihydro-2,5(1H,6H)-quinolinedione Melting point: 145°-148° C.
1-(3-methoxy-propyl)-7,8-dihydro-2,5(1H,6H)-quinolinedione Melting point: 98°-102° C.
1-propyl-7,8-dihydro-2,5(1H,6H)-quinolinedione Melting point: 69°-70° C. I-isopropyl-7,8-dihydro-2,5(1H,6H)-quinolinedione [Melting point: 110-112° C.].
1-butyl-7,8-dihydro-2,5(1H,6H)-quinolinedione [Melting point: 64°14 70° C.].
1-(2-methylpropyl)-7,8-dihydro-2,5(1H,6H)-quinolinedione oil, Rf-value: 0.65 (Polygram silica gel plates SIL G/UV254 of Messrs. Machery-Nagel, system: chloroform/ethanol=19/1 by volume).
1-tetrahydrofurfuryl-7,8-dihydro-2,5(1H,6H)-quinolinedione oil, Rf-value: 0.58 (Polygram silica gel plates SIL G/UV254 of Messrs. Machery-Nagel, system: chloroform/ethanol=19/1 by volume).
1-cyclohexyl-7,8-dihydro-2,5(1H,6H)-quinolinedione Melting point: 162°-163° C.
1-allyl-7,8-dihydro-2,5(1H,6H)-quinolinedione Melting point: 115°-117° C.
1-propargyl-7,8-dihydro-2,5(1H,6H)-quinolinedione Melting point: 208°-210° C.

EXAMPLE 35

1-Methoxycarbonylmethyl-7,8-dihydro-2,5(1H,6H)-quinolinedione

Prepared analogously to Example 29 from 7,8-dihydro- 2,5(1H,6H)-quinolinedione and methyl bromoacetate.

Melting point: 129°-130° C.

EXAMPLE 36

1-Carboxymethyl-7,8-dihydro-2,5(1H,6H)-quinolinedione

Prepared by saponification from 1-methoxycarbonylmethyl-7,8-dihydro-2,5(1H,6H)-quinolinedione in 1 N sodium hydroxide solution at room temperature. The reaction mixture was adjusted to pH 2 after two hours and extracted with ethyl acetate.

Melting point: 238°-240° C. (decomp.).

EXAMPLE I

Tablets containing 125 mo of 1-methyl-7,8-dihydro-2,5(1H,6H)-quinolinedione

| Composition: | |
|---|---|
| Active substance | 125.0 mg |
| Microcrystalline cellulose | 63.5 mg |
| Lactose suitable for tablet making | 110.0 mg |
| Magnesium stearate | 1.5 mg |
| | 300.0 mg |

Preparation:

The excipients are thoroughly mixed with the active substance and compressed to form tablets. Round biplanar tablets are obtained facetted on both sides and notched on one side.

Weight of tablet: about 300 mg.
Diameter of tablet: 10 mm.

EXAMPLE II

Coated tablets containing 125 mg of 1-methyl-7,8-dihydro-2,5(1H,6H)-quinolinedione

| Composition: | |
|---|---|
| Active substance | 125.0 mg |
| Microcrystalline cellulose | 63.5 mg |
| Lactose suitable for tablet making | 110.0 mg |
| Magnesium stearate | 1.5 mg |
| | 300.0 mg |

Preparation:

The excipients are thoroughly mixed with the active substance and compressed to form tablets. The tablets obtained are then sugar coated with conventional sugar coating suspension and subsequently with pure sugar syrup to give coated tablets weighing 390 mg in a coating pan.

Weight of tablet core: about 300 mg.
Diameter of tablet core: 10 mm.
Appearance: round, biconvex.

EXAMPLE III

Tablets containing 125 mo of 1-ethyl-3,4,7,8-tetrahydro-2,5(1H,6H)-quinolinedione

| Composition: | |
|---|---|
| Active substance | 125.0 mg |
| Lactose 75.0 mg Corn starch | 33.8 mg |
| Polyvinylpyrrolidone (Kollidon 25R) | 5.0 mg |
| Magnesium stearate | 1.2 mg |
| | 240.0 mg |

Preparation:

The active substance thoroughly mixed with lactose and corn starch is evenly moistened with the alcoholic polyvinylpyrrolidone solution, the mass is passed through a 2.5 mm mesh screen, dried and again screened through a 1.5 mm mesh. The lubricant is added to the resulting granules to produce a mixture ready for compression. The mixture is compressed to form tablets. Round biplanar tablets are obtained with facets on both sides and a notch on one side.

Weight of tablet: about 240 mg.
Tablet diameter: 9 mm.

EXAMPLE IV

Coated tablets containing 125 mo of
1-ethyl-3,4,7,8-tetrahydro-2,5(1H,6H)-quinolinedione Composition:

| Composition: | |
|---|---|
| Active substance | 125.0 mg |
| Lactose 75.0 mg Corn starch | 33.8 mg |
| Polyvinylpyrrolidone (Kollidon 25R) | 5.0 mg |
| Magnesium stearate | 1.2 mg |
| | 240.0 mg |

Preparation:

The active substance thoroughly mixed with lactose and corn starch is evenly moistened with the alcoholic polyvinylpyrrolidone solution, the mass is screened through a 2.5 mm mesh, dried and screened again through a 1.5 mm mesh. The mixture is compressed to form tablet cores. The resulting tablets are then coated with conventional sugar coating suspension and then with pure sugar syrup in a coating pan to produce coated tablets weighing 290 mg.

Weight of tablet core: about 240 mg.
Diameter of tablet core: 9 mm.
Appearance: round, biconvex.

EXAMPLE V

Granules containing
1-methyl-7,8-dihydro-2,5(1H,6H)-quinolinedione

Composition:

| (01) Active substance | 12.5% |
|---|---|
| (02) Sorbitol | 86.0% |
| (03) Silicon dioxide | 1.3% |
| (04) Magnesium stearate | 0.2% |
| | 100.0% |

Preparation:

Components (01), (02) and (03) are mixed together and granulated moist with ethanol. After drying and screening (mesh size 1.0 mm) the granules are mixed with (04) and packed into sachets. One sachet with 1 g of granules contains 125 mg of active substance.

EXAMPLES VI

Fine granules containing
1-ethyl-3,4,7,8-tetrahydro-2,5(1H,6H)-quinolinedione

Composition:

| (01) Active substance | 12.5% |
|---|---|
| (02) Polyvinylpyrrolidone | 2.8% |
| (03) Lactose | 83.0% |
| (04) Silicon dioxide | 1.2% |
| (05) Magnesium stearate | 0.5% |
| | 100.0% |

Preparation:

Ingredient (03) with a particle size of 0.2–0.45 mm is placed in a rotating coating pan. (02) is dissolved in isopropanol and then (01) and (04) are suspended. The suspension is carefully sprayed onto the lactose crystals in the pan, under a current of dry air. After drying, it is mixed with (05) and a quantity of granules corresponding to 125 mg of active substance is packed into a sachet.

EXAMPLES VII

Hard gelatin capsules containing 125 mg of
1-ethyl-3,4,7,8-tetrahydro-2,5(1H,6H)-quinolinedione Composition:

1. Weight of capsule filling:

| Active substance | 125.0 mg |
|---|---|
| Lactose $\times$ H$_2$O | 41.0 mg |
| Dried corn starch | 82.0 mg |
| Magnesium stearate | 2.0 mg |
| | 250.0 mg |

2. Granulating liquid:

| Distilled water, | q.s. |
|---|---|
| Hard gelatin capsules, size 2 | |

Preparation:

Granulating liquid:

Some of the lactose is dissolved in warmed distilled water to form an approximately 20% solution.

Granules:

The active substance, the remaining lactose and corn starch are mixed together and moistened with the granulating liquid. The mass is screened, dried and, after being screened once more, homogeneously mixed with magnesium stearate. The fine-grained final mixture is packed into size 2 hard gelatin capsules in a suitable machine.

EXAMPLE VIII

Injection solution containing 125 mo of
1-ethyl-3,4,7,8-tetrahydro-2,5(1H,6H)-quinolinedione

| Composition: | |
|---|---|
| Active substance | 125.0 mg |
| Water for injection ad | 2 ml |

Preparation:

The active substance is dissolved at ambient temperature in water for injections. The solution is filtered sterile, transferred into clean ampoules and autoclaved for 20 minutes at 121° C.

EXAMPLE IX

Injection solution containing 125 mo of
1-ethyl-3,4,7,8-tetrahydro-2,5(1H,6H)-quinolinedione

| Composition: | |
|---|---|
| Active substance | 125.0 mg |
| Polyethyleneglycol | 200.0 mg |
| Polyoxyethylene/polyoxypropylene | 100.0 mg |
| Water for injections ad | 2 ml |

Preparation:

The active substance is dissolved at ambient temperature in water for injections, in polyethyleneglycol with an average molecular weight of 600 and in polyoxyethylene/polyoxypropylene polymer. The solution is filtered sterile, transferred into clean ampoules and autoclaved for 20 minutes at 121° C.

EXAMPLE X

Injection solution containing 125 mo of
1-methyl-7,8-dihydro-2,5(1H,6H)-quinolinedione

| Composition: | |
|---|---|
| Active substance | 125.0 mg |
| Polyethyleneglycol | 200.0 mg |
| Water for injections ad | 2 ml |

Preparation:
See Example IX.

EXAMPLE XI

Suppositories containing 200 mo of
1-methyl-7,8-dihydro-2,5(1H,6H)-quinolinedione

| Composition: | |
|---|---|
| Active substance | 200.0 mg |
| Hard fat (e.g. Witepsol H 19 and Witepsol W 45) | 1,500.0 mg |

Preparation:

The hard fat is melted. At 38° C. the ground active substance is homogeneously dispersed in the melt. This is cooled to 35° C. and poured into slightly chilled suppository moulds.

EXAMPLE XII

Suppositories containing 200 mo of
1-ethyl-3,4,7,8-tetrahydro-2,5(1H,6H)-quinolinedione

| Composition: | |
|---|---|
| Active substance | 200.0 mg |
| Hard fat (e.g. Witepsol H 19 and Witepsol W 45) | 1,500.0 mg |

Preparation:
See Example XI.

EXAMPLE XIII

Syrup containing 125 mg of
1-ethyl-3,4,7,8-tetrahydro-2,5(1H,6H)-quinolinedione
per 5 ml

| Composition: | |
|---|---|
| Active substance | 2.50 g |
| Carboxymethylcellulose | 0.10 g |
| Methyl p-hydroxybenzoate | 0.05 g |
| Propyl p-hydroxybenzoate | 0.03 g |
| Sucrose 10.00 g Glycerol | 5.00 g |
| 70% sorbitol solution | 20.00 g |
| Flavouring | 0.30 g |
| Distilled water ad | 100.00 ml |

Preparation:

Distilled water is heated to 70° C. The methyl and propyl p-hydroxybenzoates and the glycerol and carboxymethylcellulose are dissolved therein with stirring. The solution is cooled to ambient temperature and the active substance is added and dissolved therein with stirring. After the sucrose, the sorbitol solution and the flavouring have been added and dissolved, the syrup is evacuated with stirring in order to eliminate air.

EXAMPLE XIV

Syrup containing 125 mg of
1-methyl-7,8-dihydro-2,5(1H.6H)-quinolinedione per 5 ml

| Composition: | |
|---|---|
| Active substance | 2.50 g |
| Carboxymethylcellulose | 0.10 g |
| Methyl p-hydroxybenzoate | 0.05 g |
| Propyl p-hydroxybenzoate | 0.03 g |
| Sucrose 10.00 g Glycerol | 5.00 g |
| 70% sorbitol solution | 20.00 g |
| Flavouring | 0.30 g |
| Distilled water ad | 100.00 ml |

Preparation:.
See Example XIII.

What is claimed is:
1. New quinolinediones of formula

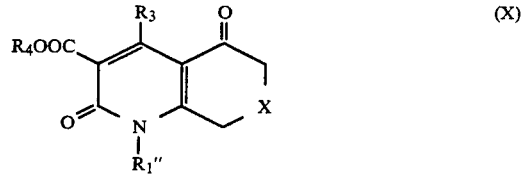

(X)

$R^3$ is hydrogen, trifluoromethyl, phenyl or $C_1$-$C_3$ alkyl,
X is methylene optionally substituted by one or two $C_1$-$C_3$ alkyl and
$R_1'''$ is hydrogen, $C_1$-$C_3$ alkyl optionally substituted by phenyl, fluorophenyl, chlorophenyl or bromophenyl, by carboxy or by $C_2$-$C_4$ alkoxycarboxyl, $C_4$-$C_6$ alkyl, $C_3$-$C_6$ cycloalkyl, $C_3$-$C_5$ alkenyl or $C_3$-$C_5$ alkynyl, a $C_2$-$C_3$ alkyl substituted in the 2- or 3- position by hydroxy, alkoxy or alkylmercapto, in which the alkoxy or alkymercapto substituent may in each case contain 1 to 3 carbon atoms, or tetrahydrofurfuryl and $R_4$ is $C_1$-$C_5$ alkyl or $R_1'''$ is $C_1$-$C_3$ alkyl optionally substituted by phenyl, fluorophenyl, chlorophenyl or bromophenyl, by carboxy or by $C_2$-$C_4$ alkoxycarboxyl, $C_4$-$C_6$ alkyl, $C_3$-$C_6$ cycloalkyl, $C_3$-$C_5$ alkenyl or $C_3$-$C_5$ alkynyl, a $C_2$-$C_3$ alkyl substituted in the 2- or 3- position by hydroxy, alkoxy or alkylmercapto, in which the alkoxy or alkylmercapto substituent may in each case contain 1 to 3 carbon atoms, or tetrahydrofurfuryl and $R_4$ is hydrogen.

* * * * *